United States Patent [19]
Juliar et al.

[11] Patent Number: 5,395,468
[45] Date of Patent: Mar. 7, 1995

[54] METHOD OF CONSTRUCTION OF A MASS TRANSFER DEVICE

[75] Inventors: Rena S. Juliar, Corona; Jeanne S. Pierson, Irvine, both of Calif.

[73] Assignee: Medtronic, Inc., Minneapolis, Minn.

[21] Appl. No.: 51,102

[22] Filed: Apr. 21, 1993

[51] Int. Cl.⁶ .................. A61M 1/18; A61M 1/24; B01D 61/00; B01D 63/02

[52] U.S. Cl. .................. 156/169; 156/74; 156/173; 156/175; 156/250; 156/256; 422/46; 422/48; 210/321.74; 210/321.83; 128/DIG. 3

[58] Field of Search ............ 156/169, 172, 174, 173, 156/175, 74, 296, 250, 256; 422/45, 46, 48; 210/321.74, 321.79, 321.83, 321.88, 497.1, 500.23; 165/172; 128/DIG. 3

[56] References Cited

U.S. PATENT DOCUMENTS

| | | |
|---|---|---|
| 3,339,341 | 9/1967 | Maxwell et al. . |
| 3,455,460 | 7/1969 | Mahon et al. ............ 210/321.88 |
| 3,475,331 | 10/1969 | McLain ................... 210/321.88 |
| 4,226,378 | 10/1980 | Fitzgerald et al. ......... 210/500.23 X |
| 4,239,729 | 12/1980 | Hasegawa et al. . |
| 4,690,758 | 9/1987 | Leonard et al. . |
| 4,715,953 | 12/1987 | Leonard . |
| 4,975,247 | 12/1990 | Badolato et al. . |
| 5,043,140 | 8/1991 | Combs ..................... 422/48 X |

FOREIGN PATENT DOCUMENTS

| | | |
|---|---|---|
| 2242129 | 3/1975 | France . |
| 2451952 | 10/1980 | France . |
| 8300098 | 1/1983 | WIPO ................. 210/321.83 |
| 9004419 | 5/1990 | WIPO . |

Primary Examiner—Jeff H. Aftergut
Attorney, Agent, or Firm—Michael J. Jaro; Harold R. Patton

[57] ABSTRACT

A mass transfer device and method of construction thereof. The mass transfer device may be an oxygenator having a fiber bundle comprised of hollow gas permeable fibers. The method of making the fiber bundle used in the mass transfer device includes winding one or more hollow fibers around a supporting core which includes first and second core sections. First and second outer casing sections are mounted adjacent the exterior of the hollow fibers. The hollow fibers are then cut longitudinally in two circumferentially spaced locations to form first and second fiber bundles located between the first and second core and outer casing sections. The method results in the simultaneous construction of first and second fiber bundles which are useable in separate mass transfer devices.

21 Claims, 9 Drawing Sheets

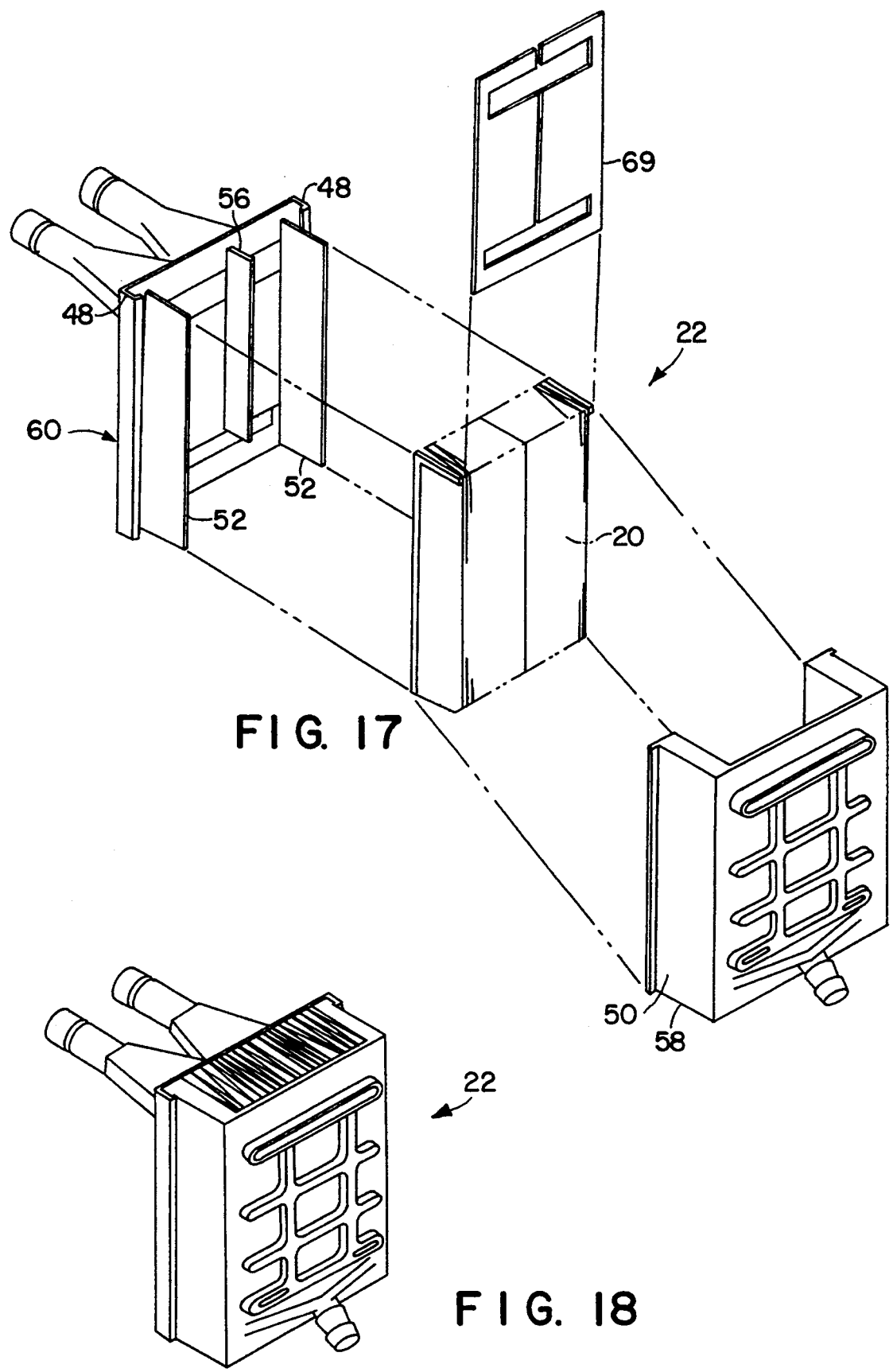

METHOD OF CONSTRUCTION OF A MASS TRANSFER DEVICE

FIELD OF THE INVENTION

The present invention relates to a mass transfer device and method of construction thereof in which substances contained in fluids flowing on opposite sides of a microporous membrane are exchanged for each other by molecular transfer across the membrane. More particularly, the invention relates to an oxygenator having a fiber bundle comprised of hollow gas permeable fibers and the method in which the oxygenator and the fiber bundle are constructed.

BACKGROUND OF THE INVENTION

Mass transfer devices are used in various medical applications where it is necessary to effect a molecular transfer from one fluid to another. Examples are dialyzers and blood oxygenators.

Blood oxygenator systems are widely used in open heart surgeries and for providing emergency cardiopulmonary assistance. In both cases, the oxygenator takes over, either partially or completely, the normal gas exchange function of the patient's lung. In oxygenators which employ a microporous membrane, blood is taken from the patient and is circulated extracorporeally through the oxygenator on one side of the membrane. Carbon dioxide is transferred from the blood across the microporous membrane into the passing stream of oxygenating gas. At the same time, oxygen is transferred from the oxygenating gas across the membrane into the blood. The circulating blood, having thereby been reduced in carbon dioxide content and enriched in oxygen, is returned to the patient. Blood is circulated, oxygenated and returned to the patient in the aforementioned manner until the patient's own cardiopulmonary system is once more able to carry out its normal circulatory and gas exchange functions.

Several types of blood oxygenators have been or are generally available. One type is a bubble oxygenator wherein the oxygenating gas is introduced into the blood directly in the form of bubbles. In a second type of oxygenator, called a film-type oxygenator, a thin blood film is made and gas exchange takes place on the surface of the exposed blood film. A third type of blood oxygenator is called a membrane oxygenator. In the membrane oxygenator, the blood is separated from direct contact with the oxygenating gas by a membrane. This membrane must be microporous or semipermeable, that is, the membrane must be capable of permitting carbon dioxide and oxygen to permeate through it while at the same time preventing the fluid itself from passing therethrough.

There are two main types of membrane blood oxygenators currently available. One type, called the flat plate membrane oxygenator, employs one or more thin, flat sheets of microporous membrane. In its most basic form the flat plate oxygenator has a single sheet of microporous membrane sealed into a housing so as to provide in the housing a blood compartment for the flow of blood and a separate gas compartment for the flow of an oxygenating gas. Each of the compartments is fitted with an inlet and an outlet. Blood flows into and out of the blood compartment and the oxygenating gas flows into and out of the gas compartment. Oxygen passes from the oxygenating gas across the membrane into the blood flowing through the blood compartment. Carbon dioxide passes from the entering blood across the membrane to be entrained in the oxygenating gas. The exiting blood, now reduced in carbon dioxide and enriched in oxygen, is returned to the patient.

The other main type of membrane oxygenator is the hollow fiber oxygenator which may be constructed in several different ways. One construction type is illustrated generally in U.S. Pat. No. 4,239,729 to Hasegawa et al. A hollow fiber oxygenator employs a large number (typically, thousands) of microporous or semipermeable hollow fibers disposed within a housing. These hollow fibers are sealed in the end walls of the housing which are then fitted with skirting end caps. One end cap is fitted with an inlet and the other end cap is fitted with an outlet. The peripheral wall of the housing has an inlet located interiorly of one of the end walls and an outlet located interiorly of the other end wall. In the Hasegawa et al. oxygenator, the hollow fibers are aligned in the housing so that their longitudinal axes are generally parallel to the longitudinal axis of the housing. Blood enters through the inlet of one end cap, passes through the lumens of the hollow fibers, and exits through the outlet of the other end cap. The oxygenating gas enters the device through the inlet in the peripheral wall near one end of the device, passes over the outer surfaces of the hollow fibers, and exits the device through the outlet in the peripheral wall near the other end of the device. It will be understood that carbon dioxide diffuses from the blood flowing inside the hollow fibers through the fiber walls into the stream of oxygenating gas. At the same time, oxygen from the oxygenating gas flowing over the outer surfaces of the hollow fibers diffuses through the walls of the hollow fibers into the lumens thereof to oxygenate the blood flowing therethrough.

Another type of hollow fiber oxygenator utilizes a spirally wound hollow fiber bundle. This type hollow fiber oxygenator is illustrated in U.S. Pat. No. 4,975,247 to Badolato et al. The Badolato et al. oxygenator includes a hollow fiber bundle having first and second ends located within an oxygenator chamber. The oxygenator chamber includes a hollow core around which the hollow fibers are spirally wound and an outer casing adjacent the fibers. A gas entry port is coupled to the interior of the fibers adjacent the first end of the bundle and a gas outlet is coupled to the interior of the fibers at the second end of the bundle. A blood inlet to the oxygenator chamber, exterior of the fibers, is provided adjacent the second end of the bundle, and a blood outlet from the oxygenator chamber is provided adjacent the first end of the bundle. In contrast to the fluid flow pattern of the Hasegawa et al. oxygenator, in the Badolato et al. oxygenator, carbon dioxide diffuses from the blood flowing over the outer surfaces of the hollow fibers through the fiber walls into the stream of oxygenating gas flowing through the lumens of the hollow fibers. At the same time, oxygen from the oxygenating gas flowing inside the hollow fibers diffuses through the walls of the hollow fibers to oxygenate the blood flowing over the outer surfaces of the hollow fibers.

Another example of a spirally wound oxygenator is illustrated in U.S. Pat. No. 4,690,758 to Leonard et al.

In the past, fiber bundles for spirally wound mass transfer devices including oxygenators have typically been made by winding hollow fibers circumferentially around a generally cylindrical core. The winding is repeated until the desired bundle thickness is obtained.

This results in a generally cylindrical fiber bundle. The interiors of the fibers are then accessed in some manner so that an inlet and outlet may be added in order to provide a fluid flow path through the lumens of the fibers. In the Badolato et al. oxygenator this was done by embedding the fiber bundle at its top and bottom ends in a solidified potting composition and then cutting a portion of the top and bottom ends of the bundle to expose the lumens of the fibers. The same general procedure is utilized in U.S. Pat. No. 4,690,758 to Leonard et al.

In U.S. Pat. No. 4,715,953 to Leonard a hollow fiber separation device is disclosed in which the lumens of the fibers are accessed in a different manner. In this device hollow fibers are circumferentially wrapped about a core which is typically cylindrical and hollow to form a fiber bundle. The fiber bundle is then impregnated with a potting compound and centrifuged until the potting compound is cured. A longitudinal space is cut through the circumferentially wrapped bundle at the potted band, exposing open ends of the hollow fibers at opposed sides of the space. The resulting shape of the bundle of hollow fibers wrapped about the core typically assumes the configuration of a split ring.

Regardless of the manner in which the fiber bundles are constructed or the method used to access the lumens of the fibers, the method of construction has typically been complicated, time consuming and somewhat wasteful of materials. For example, in those oxygenators where the lumens of the fibers are accessed at the top and bottom ends of the cylindrical bundle two potting steps and two cutting steps are required resulting in additional construction time and in waste of materials. Although in Leonard U.S. Pat. No. 4,715,953, only one potting and cutting step is required, a significant amount of fiber is cut away as waste. Additionally, the resulting structure wherein the gas inlet and outlet are combined into one manifold is undesirable in that communication leaks between the gas meet and outlet can develop compromising the efficiency and safety of the oxygenator.

In view of the disadvantages in the construction and operation of prior art spirally wound hollow fiber bundles currently used in mass transfer devices, a mass transfer device utilizing a hollow fiber bundle which can be constructed efficiently from both a time and material standpoint would be desirable.

SUMMARY OF THE INVENTION

In accordance with the present invention there is disclosed an improved mass transfer device and method of construction. In one aspect the invention is a method of making fiber bundles for use in a hollow fiber separation devices. The method comprises winding one or more hollow fibers circumferentially around a supporting core. The supporting core includes a first core section and a second core section which define a longitudinal axis about which the fibers are wound. First and second outer casing sections are mounted adjacent the exterior of said hollow fibers. The hollow fibers are then cut in at least two circumferentially spaced locations such that said hollow fibers are divided into a plurality of fiber bundles including a first fiber bundle lying generally between the first outer casing and the first core section and a second fiber bundle lying generally between the second outer casing and the second core section. Each of the fiber bundles has the interior of the hollow fibers of which it is made exposed along a first end and a spacially separated second end. Both the first and second fiber bundles are thus constructed at the same time by use of the method of this invention and may be used in separate hollow fiber separation devices.

In this aspect of the invention the supporting core may be substantially cylindrical. Additionally, the step of cutting through the hollow fibers may be made in a direction substantially parallel to the longitudinal axis of the supporting core. The step of cutting through said fibers may also be made in a direction substantially coinciding with a plane through the longitudinal axis of the supporting core such that the first and second fiber bundles are substantially identical in size and shape.

In another aspect the invention is a method of making a hollow fiber separation device. The method comprises winding at least one hollow fiber around a supporting core which may be cylindrical. The supporting core has an exterior surface about which the hollow fiber is wound which defines a longitudinal axis extending therethrough. An outer casing is mounted adjacent the exterior of the hollow fibers. The hollow fibers are then cut in at least two circumferentially spaced locations to form a fiber bundle having a first cut end at which the interiors of a first end of the hollow fibers are exposed and a second cut end at which the interiors of a second end of the hollow fibers are exposed. The area between the first cut ends of the hollow fibers in the fiber bundle are then sealed. The area between the second cut ends of the hollow fibers in the fiber bundle are similarly sealed. Preferably the steps of sealing between the first and second cut ends of the hollow fibers are performed simultaneously. The seal between the first and second cut ends of the fiber bundle and the core section and the casing section together define a molecular transfer chamber. First fluid inlets are coupled to the interior of the hollow fibers at the first cut ends of the hollow fibers in the fiber bundle and first fluid outlets are coupled to the interior of the hollow fibers at the second cut ends of the hollow fibers in the fiber bundle. Second fluid inlets are coupled to the molecular transfer chamber for allowing a second fluid to enter the molecular transfer chamber. Second fluid outlets are coupled to the molecular transfer chamber for allowing the second fluid to exit from the molecular transfer chamber. The step of cutting may be accomplished in a manner which results in the fiber bundle being shaped such that the first and second cut ends of the fiber bundle and the longitudinal axis of the supporting core lie generally in a common plane. The cutting may also be made in a direction substantially parallel to the longitudinal axis of the supporting core.

In one embodiment the invention is a method of making hollow fiber bundles for use in oxygenators. The oxygenators in which the fiber bundles may be used have an outer casing and a core section between which is an oxygenation chamber which houses the fiber bundle. A gas inlet is operatively coupled to the interior of the hollow fibers at a first end of the fiber bundle and a gas outlet is operatively coupled to the interior of the hollow fibers at a second end of the fiber bundle which is spacially separated from the first end of the fiber bundle. A blood inlet and a blood outlet operatively coupled to the oxygenation chamber for allowing blood to enter and exit from the oxygenation chamber. In this embodiment the method comprises winding one or more hollow gas permeable fibers around a support core. The support core includes a first core section and a second core section and defines a longitudinal axis extending between the core sections and about which the hollow fibers are wound. A first outer casing and a second outer casing are mounted adjacent to the hollow gas permeable fibers such that the hollow gas permeable fibers are between the first and second outer casings and the support core. The hollow gas permeable fibers are cut in at least two circumferentially spaced locations such that the fibers are divided into a first hollow fiber bundle lying generally between the first outer casing and the first core section and a second hollow fiber bundle lying generally between the second outer casing and the second core section. The method results in the simultaneous construction of first and second fiber bundles which are useable in separate oxygenators. The step of cutting through said fibers may be made in a direction substantially coinciding with a plane through the longitudinal axis of the supporting core such that the first and second fiber bundles are substantially identical in size and shape. The step of cutting through the hollow fibers may also be made in a direction substantially parallel to the longitudinal axis of said support core.

A further embodiment of the invention consists of a method of making an oxygenator. In this embodiment the method comprises winding at least one gas permeable hollow fiber around a supporting core. The supporting core has a longitudinal axis which is defined by the outer surface of the supporting core about which the hollow fibers are wound. An outer casing is mounted around the exterior of the hollow fibers. The hollow fibers are cut in at least two circumferentially spaced locations to form a fiber bundle having a first cut end at which the interiors of a first end of the hollow fibers are exposed and a second cut end at which the interiors of a second end of the hollow fibers are exposed. The area between the first cut ends of the hollow fibers in the fiber bundle is sealed. The area between the second cut ends of the hollow fibers in the fiber bundle are similarly sealed. Preferably and advantageously the steps of sealing between the first and second cut ends of the hollow fibers are performed simultaneously. The seal between the first and second ends of the fiber bundle and the supporting core section and the casing section together define an oxygenation chamber. A gas inlet is coupled to the interior of the hollow fibers at the first cut ends of the hollow fibers in the fiber bundle and a gas outlet is coupled to the interior of the hollow fibers at the second ends of the hollow fibers in the fiber bundle. A blood inlet is coupled to the oxygenation chamber for allowing blood to enter the oxygenation chamber and a blood outlet to the oxygenation chamber for allowing blood to exit from the oxygenation chamber. The step of cutting may be done in a direction which results in the fiber bundle being shaped such that the first and second cut ends of the fiber bundle and the longitudinal axis of the supporting core lie generally in a common plane. The step of cutting may also be made in a direction substantially parallel to the longitudinal axis of the supporting core. The method may also include mounting an optional heat exchanger within the outer casing. The heat exchanger is provided with a blood entry and blood exit. The blood exit from the heat exchanger is positioned and arranged in fluid communication with the blood inlet of the oxygenator.

In still a further embodiment the invention is a method of making an oxygenator. The method comprises winding at least one gas permeable hollow fiber around a supporting core. The supporting core includes first and second core sections which define a longitudinal axis extending between the core sections and about which the hollow fibers are wound. An outer casing is mounted around the exterior of the hollow fibers. The outer casing has a first casing section and a second casing section. The hollow fibers are cut in at least two circumferentially spaced locations such that said fibers are divided into a plurality of fiber bundles including first and second fiber bundles. The first and second fiber bundles each have a first cut end at which the interiors of a first end of the hollow fibers are exposed and a second cut end at which the interiors of a second end of the hollow fibers are exposed. The first fiber bundle is positioned generally between the first casing section and the first core section and the second fiber bundle is positioned generally between the second casing section and the second core section. The first fiber bundle, the first core section and the first casing section together form a first oxygenator. The second fiber bundle, the second core section and the second casing section together form a second oxygenator. The area between the first ends of the hollow fibers in the first and second fiber bundles is sealed. Similarly, the area between the second ends of the hollow fibers in the first and second fiber bundles is sealed. Preferably, the steps of sealing between the first and second cut ends of said hollow fibers are performed simultaneously. The sealed areas at the cut ends of the hollow fibers in the first fiber bundle, the first core section and the first casing section together define a first oxygenation chamber in the first oxygenator. The sealed areas at the cut ends of the hollow fibers in the second fiber bundle, the second core section and the second casing section together defining a second oxygenation chamber in the second oxygenator. Gas inlets are coupled to the interior of the hollow fibers at the first cut ends of the hollow fibers in the first and second hollow fiber bundles and gas outlets are coupled to the interior of the hollow fibers at the second cut ends of the hollow fibers in the first and second fiber bundles. Blood inlets are coupled to the first and second oxygenation chambers for allowing blood to enter the oxygenation chambers. Blood outlets are coupled to the oxygenation chambers for allowing blood to exit from the oxygenation chambers. The step of cutting may be done in a direction which results in the first and second fiber bundles being shaped such that the first and second cut ends of the first and second fiber bundles and the longitudinal axis of the supporting core lie generally in a common plane. The step of cutting through the hollow fibers may be made in a direction substantially parallel to the longitudinal axis of the supporting core. The method may include mounting an optional heat exchanger within the outer casing. The heat exchanger is provided with a blood entry and blood exit. The blood exit from said heat exchanger is positioned and arranged in fluid communication with the blood inlet of the oxygenators.

In another embodiment the invention comprises a hollow fiber oxygenator. The oxygenator comprises a hollow fiber bundle wound helically around a supporting core. The supporting core has a longitudinal axis about which the hollow fibers are wound. The fiber bundle comprises hollow, gas permeable fibers, each hollow fiber having a first end, a second end and a hollow interior. The first and second ends of the hollow fibers and the longitudinal axis of the supporting core lie generally in a common plane. An outer casing is mounted adjacent to the fiber bundle. First sealing means are provided for sealing between the first ends of the hollow fibers in the fiber bundle and sealing the hollow fibers to the supporting core and the outer casing. Second sealing means are provided for sealing between the second ends of the hollow fibers in the fiber bundle and sealing the hollow fibers to the supporting core and to the outer casing such that the first and second sealing means, said support core and said outer casing together define an oxygenation chamber. A gas inlet is operatively coupled to the interior of the hollow fibers at the first ends of the hollow fibers and a gas outlet is operatively coupled to the interior of the hollow fibers at the second ends of the hollow fibers. A blood inlet is operatively coupled to the oxygenation chamber and a blood outlet is operatively coupled to the oxygenation chamber, such that blood enters the oxygenation chamber through the blood inlet, flows through the fiber bundle and exits the oxygenation chamber through the blood outlet. The hollow fiber oxygenator of this embodiment may further comprise an optional heat exchanger having blood entry means and blood exit means for allowing blood to enter and exit the heat exchanger. The blood exit means is positioned and arranged in fluid communication with the blood inlet.

DESCRIPTION OF THE DRAWINGS

FIG. 17 is an exploded perspective view of the heat exchanger showing the interrelationship of the elements of the heat exchanger portion of the oxygenator of FIG. 1.

FIG. 18 is a perspective view of the assembled heat exchanger portion of the oxygenator of FIG. 1.

DETAILED DESCRIPTION OF THE INVENTION

Figure 1:
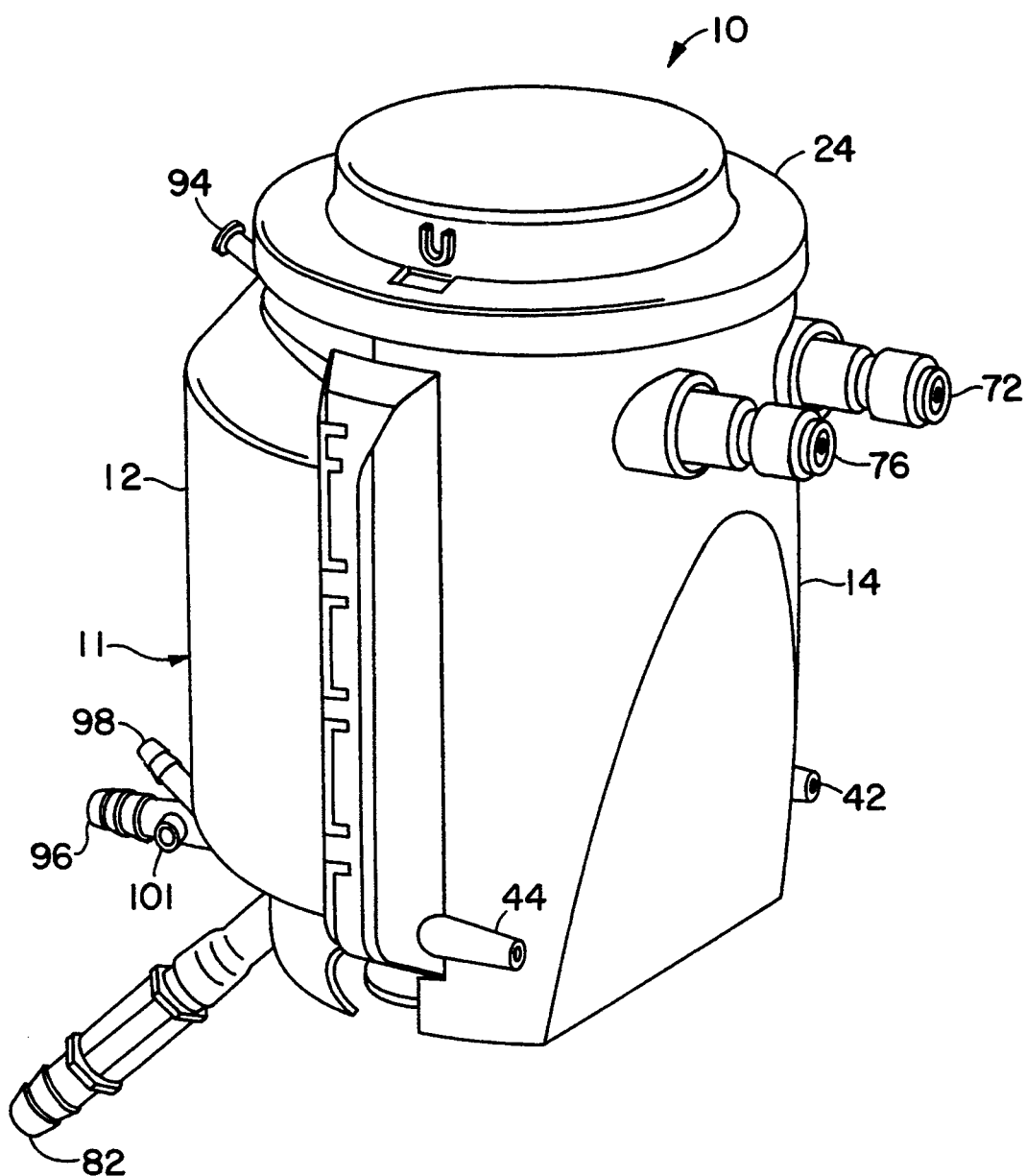
FIG. 1 is a perspective view of a hollow fiber oxygenator is accordance with the present invention.
Figure 2:
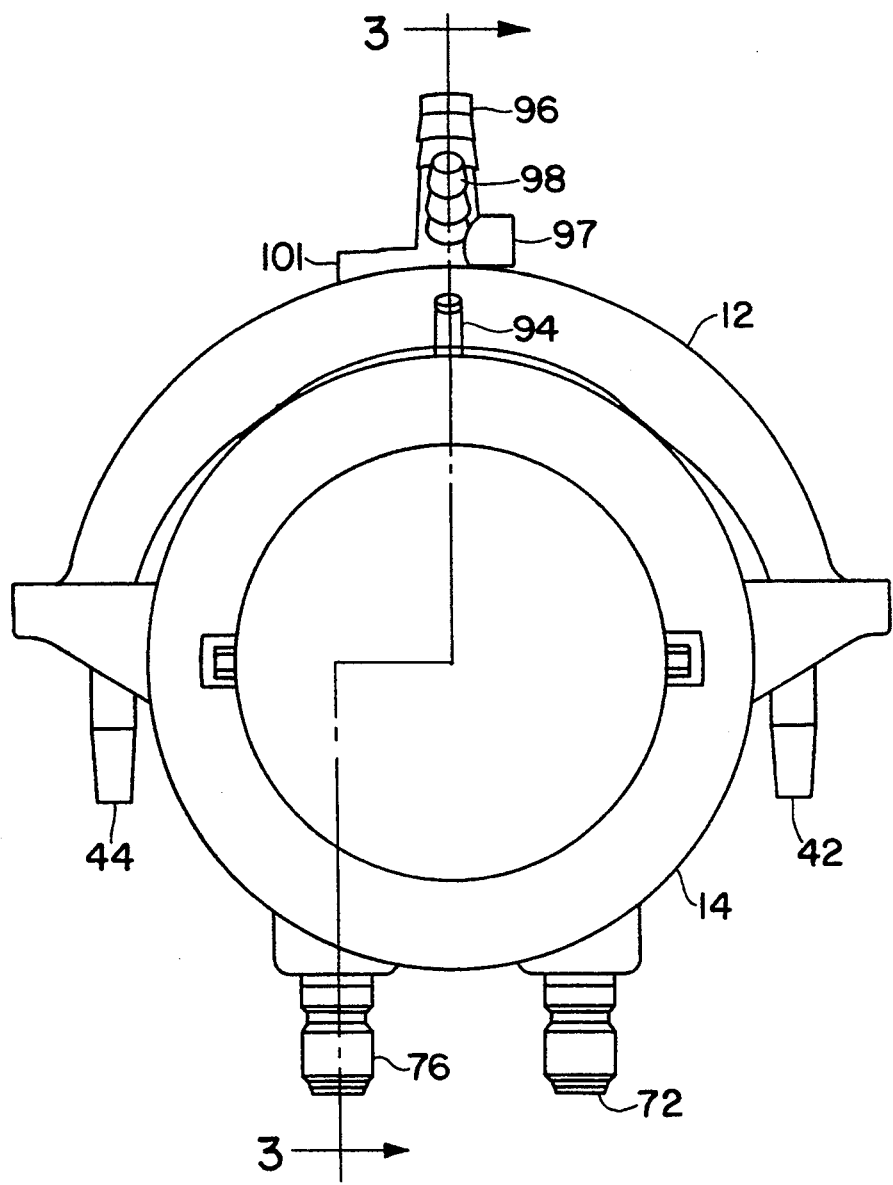
FIG. 2 is a top view of the oxygenator of FIG. 1.

With reference to FIGS. 1 through 5, a blood oxygenator 10 in accordance with the present invention is illustrated. It should be noted that although the preferred embodiment shown in the drawings is of an oxygenator, the device and methods of the present invention have applicability to other mass transfer devices which utilize hollow fiber bundles to effect a molecular transfer from one fluid to another. For example, the present invention includes the methods disclosed herein may be used in making fiber bundles for use in either oxygenators or other hollow fiber separation devices such as dialyzers.

Figure 3:
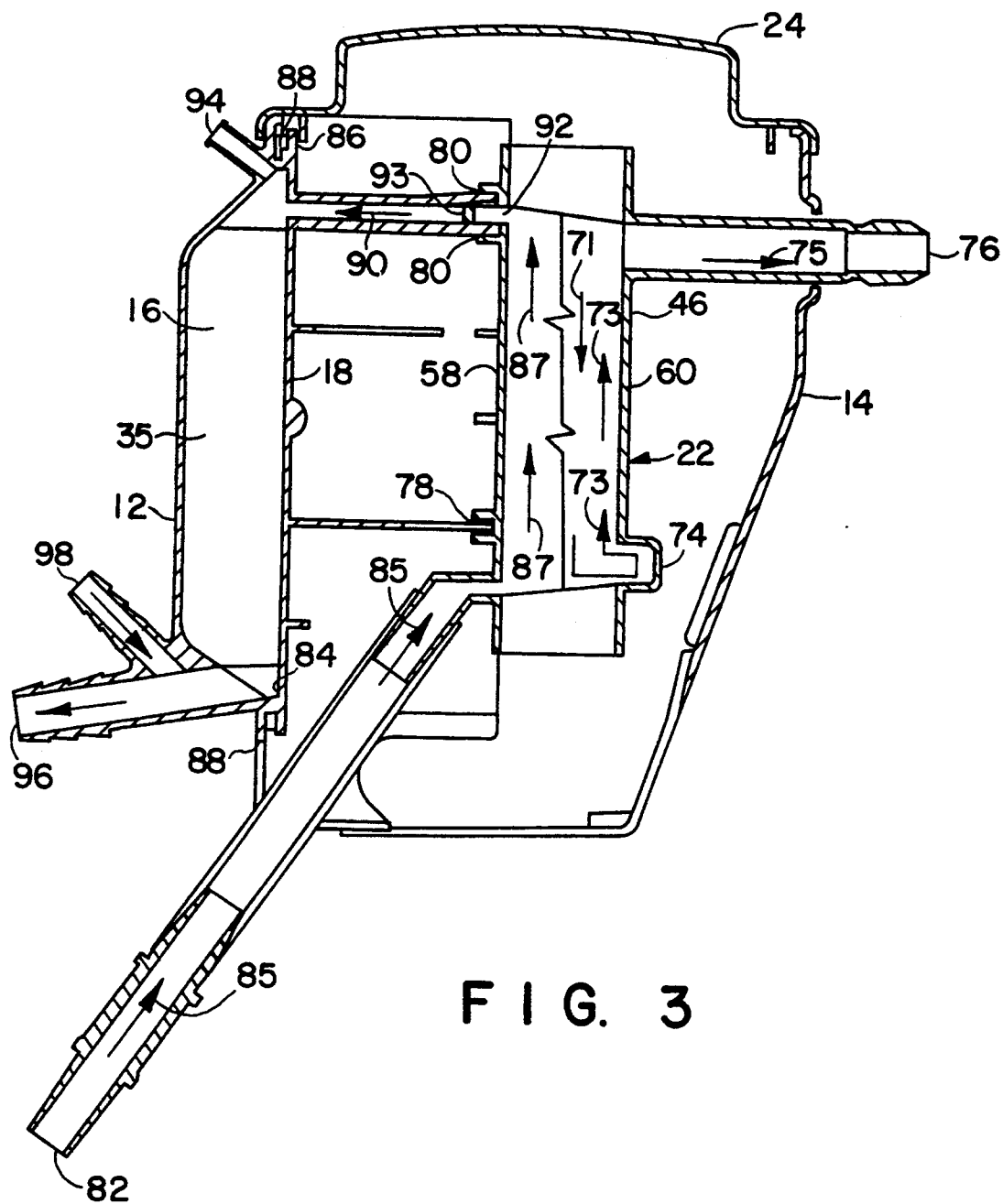
FIG. 3 is a sectional view taken along line 3—3 of FIG. 2.
Figure 4:
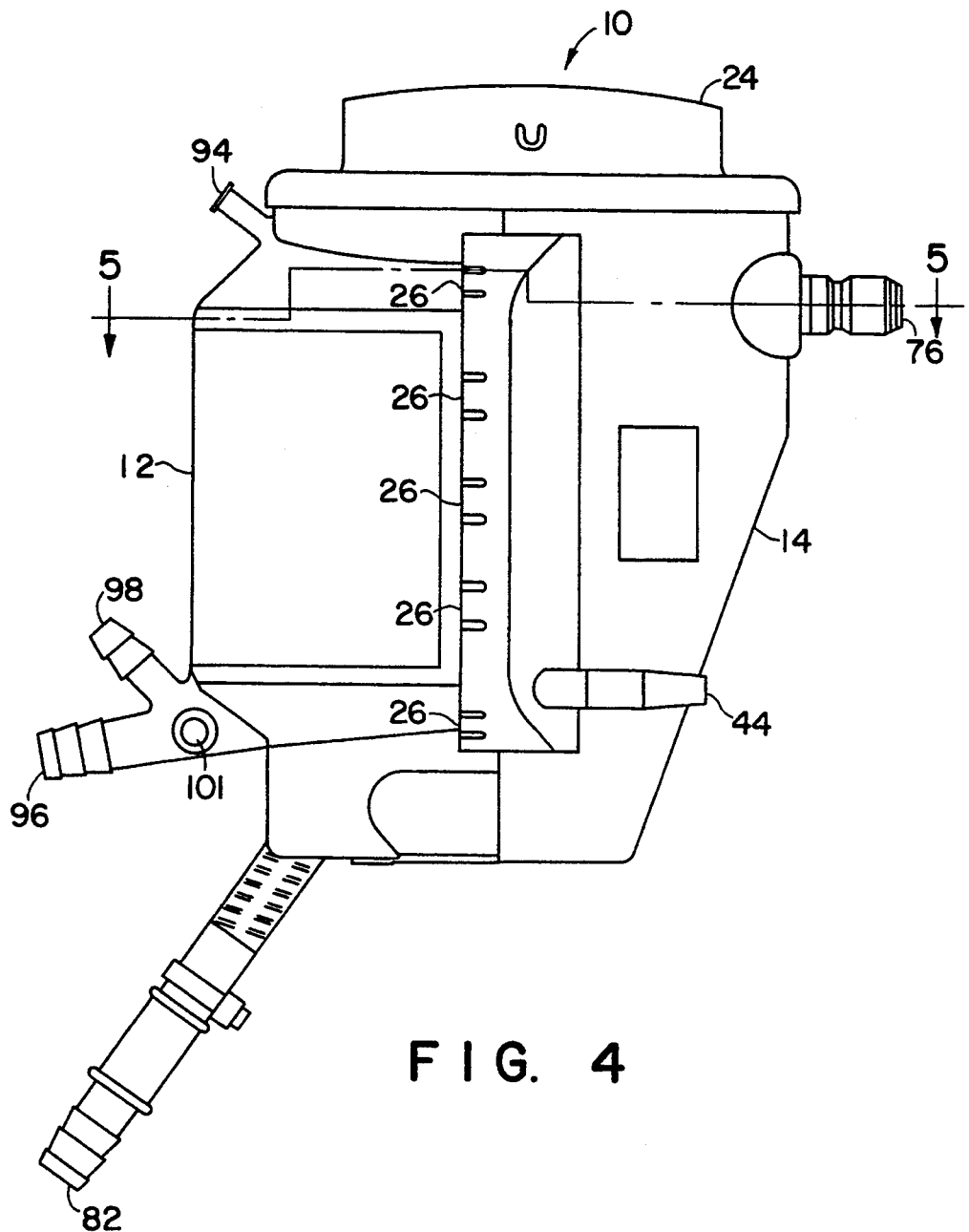
FIG. 4 is a side view of the oxygenator of FIG. 1.
Figure 5:
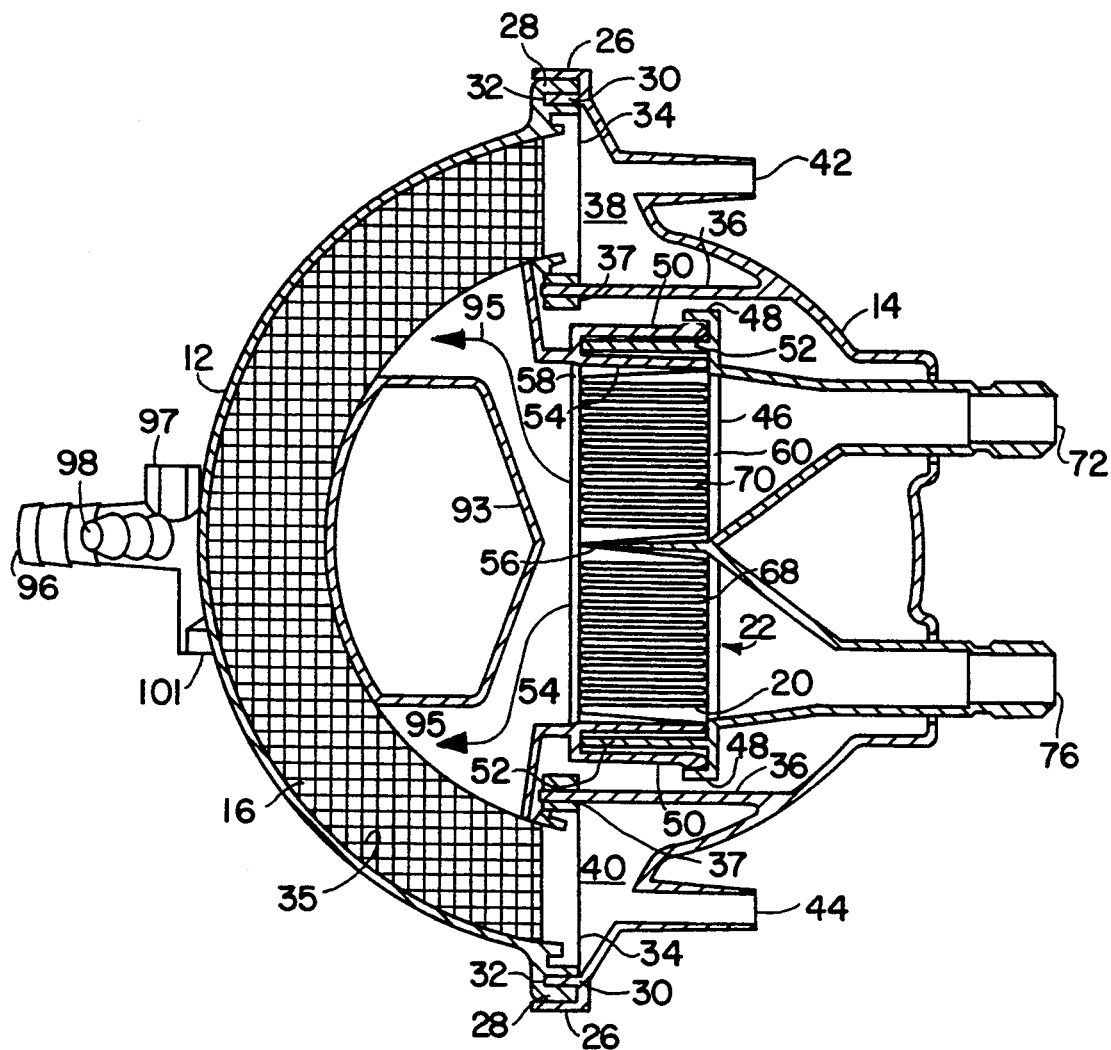
FIG. 5 is a sectional view taken along line 5—5 of FIG. 4.

As viewed in FIG. 1, oxygenator 10 has a generally cylindrical outer casing 11 having two mating case portions 12 and 14. Oxygenator 10 includes a hollow fiber bundle 16 being generally in the shape of a half cylinder contained between case portion 12 and an inner core 18 as best illustrated in FIGS. 3 and 5. Hollow fiber bundle 16 is comprised of multiple hollow fibers which are formed by winding continuous semipermeable hollow fibers around two inner cores 18 until the desired bundle thickness is attained. The bundle is then cut in a manner which will be explained in more detail hereafter with reference to FIGS. 6–16. Heat exchanger 22 is optionally included as an integral portion of oxygenator 10 and consists of corrugated stainless steel formed into a series of pleats 20 contained within a rectangular pack as will be more fully described with respect to FIGS. 17 and 18. Alternatively, heat exchanger 22 may be constructed as a separate unit. The oxygenator is equipped with a top end cap 24 which is fitted over outer casing portions 12 and 14.

With particular reference to FIG. 5, case portions 12 and 14 are snap fitted together by engagement of snap fitting tabs 26 located along the lateral edges of case portion 14 with flanges 28 which extend along the lateral edges of case portion 12. The fitting between case portions 12 and 14 includes laterally extending tongues 30 on case portion 14 which mate with accommodating grooves 32 on case portion 12. During construction the fittings are sealed with a u.v. curable adhesive or, alternatively, with a urethane potting compound.

With continued reference to FIG. 5, potted areas 34 extend along the open fiber edges of fiber bundle 16. Potted areas 34 seal the space between the hollow fibers at each end of fiber bundle 16 and together with case portion 12 and inner core 18 define an enclosed oxygenating chamber 35. Case portion 14 includes manifold sections 36 which mate with manifold grooves 37. Sections 36 and grooves 37 are sealed a u.v. curable adhesive or a urethane potting compound. Case portion 14 together with manifold sections 36 and potted areas 34 define gas inlet manifold 38 and gas outlet manifold 40. In operation, oxygenating gas enters gas inlet manifold 38 through gas inlet port 42, travels through the interiors of the hollow fibers to gas outlet manifold 40 and exits through gas outlet port 44.

With reference to FIGS. 3, 5, 17 and 18 blood oxygenator 10 includes heat exchanger 22 which is contained within a rectangular housing 46. Housing 46 includes inner section 58 which is snap fitted together with outer section 60. Outer section 60 includes snap fitting tabs 48 and interlocking walls 52. Inner section 58 includes notched sides 50 and interlocking walls 54. Snap fitting tabs 48 engage notched sides 50 to lock sections 58 and 60 together. The pleats of heat exchanger 22 extend between notched sides 50 and interlocking walls 52 and 54 to anchor the heat exchanger is a fixed position. Heat exchanger 22 is divided into two sections 68 and 70 by center divider 56 which is part of outer section 60. A resilient spacer 69 is positioned between pleats 20 and inner section 58 to ensure that pleats 20 fit snugly within rectangular housing 46 as shown in FIG. 17. The top and bottom portions of heat exchanger 22 are sealed with a urethane potting material 62 in order to seal the fluid flow paths.

The flow of water through heat exchanger 22 can be understood with reference to FIG. 3 which is a side sectional view of oxygenator 10. Water enters heat exchanger 22 through water inlet port 72 (not shown in FIG. 3) and flows down section 70 in the direction of arrow 71 to crossover channel 74. Crossover channel 74 provides a fluid flow path to section 68. The water flows through crossover channel 74 and up section 68 as illustrated by arrow 73 and flows through water outlet port 76 (arrow 75) where it exits heat exchanger 22.

With continued reference to FIG. 3 the flow of blood through blood oxygenator 10 will be explained. Heat exchanger 22 is connected to inner core 18 at tongue and groove joint 78 and oval joint 80. Inner core 18 is connected to case portion 12 at joints 84 and 86. Joints 78, 80, 84 and 86 are attached and sealed with a u.v. curable adhesive or a urethane potting material 88. In operation, blood enters the bottom portion of heat exchanger 22 through blood inlet port 82 as illustrated by arrow 85. The blood flows up sections 68 and 70 of heat exchanger 22 on the side of the pleats opposite the water in the direction of arrows 87. The blood and water flow paths are completely separated by the urethane potting material 62 at the top and bottom of the heat exchanger. Additionally, both sides of rectangular housing 46 may be sealed with urethane potting material between notched sides 50, and interlocking walls 52 and 54. As the blood flows upwardly in heat exchanger 22 it will be apparent that it is flowing in a countercurrent direction to the water in section 70 of the heat exchanger and in a co-current direction in section 68. As the blood reaches the top of heat exchanger 22 it exits the heat exchanger through an elongated opening 92 and travels through blood flow path 90 and into oxygenating chamber 35. As shown in FIG. 5, blood flow path 90 branches out around a baffle 93 to provide two separate flow paths illustrated by arrows 95 which blood may follow in reaching fiber bundle 16. This provides for an even distribution of blood to fiber bundle 16 which enhances the efficiency of gas exchange and minimizes low flow or stagnant areas.

As illustrated in FIG. 5, as the blood enters oxygenating chamber 35 it changes directions to flow downwardly through fiber bundle 16. This change of direction tends to cause any air bubbles which may be present in the blood to rise. An air purge port 94, as best seen in FIG. 3, is provided at the top of oxygenating chamber 35 to purge air from the system. As the blood flows down through fiber bundle 16 it passes over the exterior of the hollow fibers and is oxygenated by the oxygenating gas flowing through the lumens of the hollow fibers. The oxygenated blood exits oxygenator 10 through blood outlet port 96 so that it can be returned to the patient. Oxygenator 10 also includes recirculation port 98, a luer fitting 97 for taking arterial blood samples, and a thermo well 101 which accepts a temperature transducer for measuring blood temperature.

Figure 7:
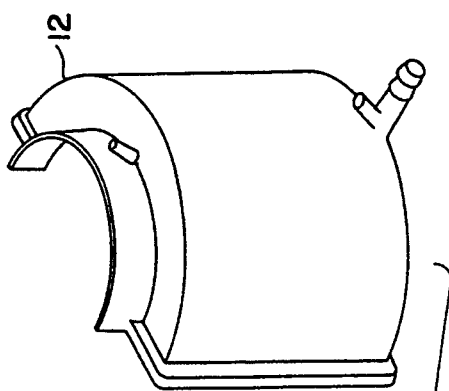
FIGS. 6 through 16 are perspective views reduced in size and omitting some construction detail which illustrate the steps in the construction of the oxygenator of FIG. 1.
Figure 6:
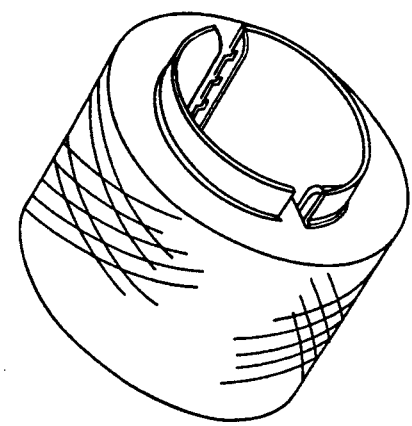
Figure 8:
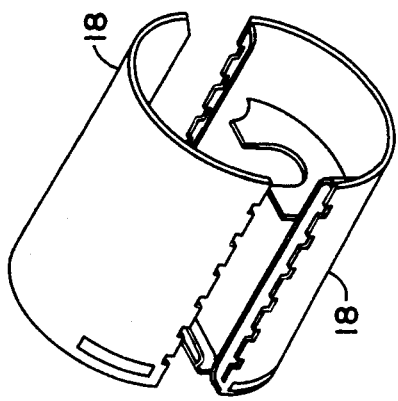
Figure 8:
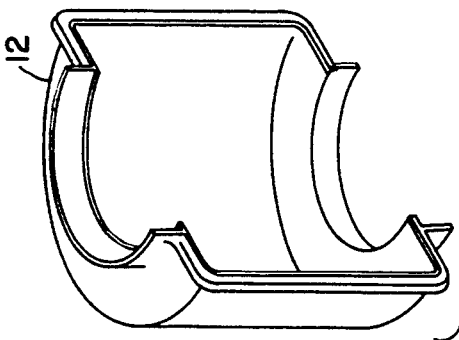
Figure 9:
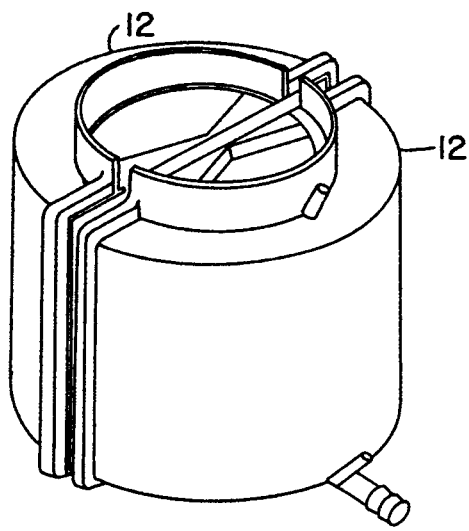
Figure 10:
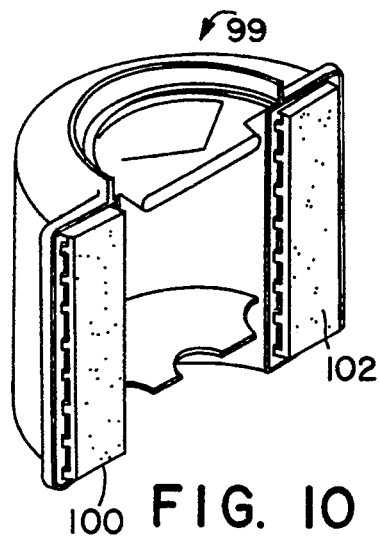
Figure 11:
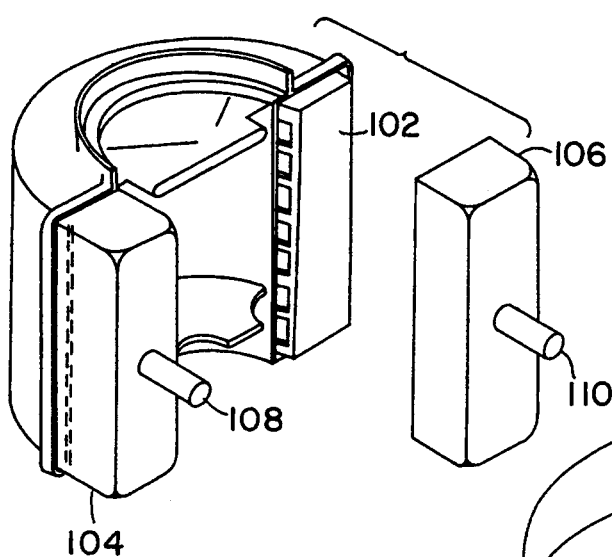

The manner of construction of oxygenator 10 will now be explained with reference to FIGS. 6 through 16 which detail step by step the procedure followed in constructing the oxygenator. As illustrated in FIG. 6, the procedure begins by starting with a supporting core consisting of two inner cores 18. Inner cores 18 are attached to a winding mandrel (not shown) which holds cores 18 in a fixed and slightly separated relationship to one another. A ribbon of six continuous semipermeable hollow fibers is then wound around inner cores 18 as shown in FIG. 7 to form a generally cylindrical fiber bundle. The manner of winding is similar to that disclosed in U.S. Pat. No. 4,975,247 issued Dec. 4, 1990, to Badolato et al., and entitled "Mass Transfer Device Having a Microporous, Spirally Wound Hollow Fiber Membrane", which is assigned to Medtronic, Inc., the assignee of the present invention the disclosure of which is hereby incorporated by reference in its entirety. Alternatively, the fiber bundle could be formed from hollow fibers bound together in mat form. The mat is then wound or wrapped around inner cores 18 until the desired depth is achieved. After the fiber bundle is wound case portions 12 are then attached to inner cores 18 with a u.v. curable adhesive (FIGS. 8 and 9). The fiber bundle is then cut into two sections in the area between inner cores 18. The angle of the direction of cut may be chosen to obtain a fiber bundle of shape. Generally, the cut is made in a direction paralled to the longitudinal axis between inner cores 18. Preferably, the fiber bundle will be cut so that the cut ends of the fibers on both sides of the fiber bundles lie in a common plane with the longitudinal axis between inner cores 18 so that the resulting portions, including fiber bundles 16, will be of equal dimension. One of the resulting cut portions 99 is shown in FIG. 10 and the remainder of the procedure in constructing the oxygenator will be explained with respect to that portion. It should be understood, however, that the same steps illustrated in FIGS. 11 through 16 may be followed with respect to the other cut portion so that a second oxygenator may be constructed by following the same steps.

Figure 12:
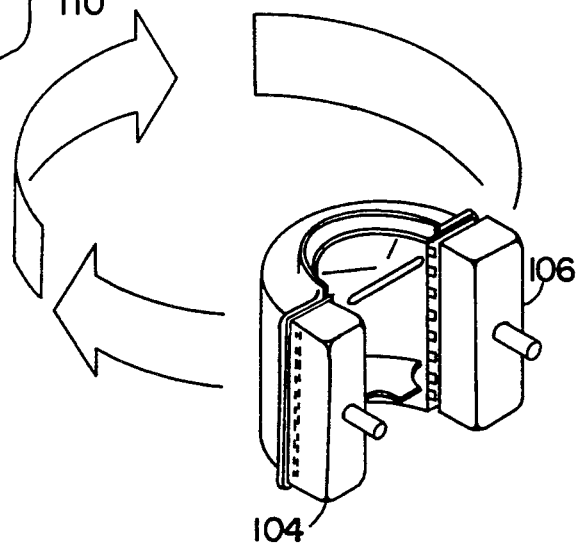

The cut ends 100, 102 of the hollow fibers which are exposed after the cutting step are then sealed by heating the ends causing them to meet and close (FIG. 10). Next, potting caps 104 and 106 are attached to cut ends 100 and 102 (FIG. 11) and a urethane potting compound is injected through ports 108 and 110. Since the ends of the hollow fibers have been sealed the potting compound does not flow into the interiors of the fibers but only between the exterior of the fibers. The unit is then centrifuged in a conventional manner as shown in FIG. 12 while the potting compound cures. The potting compound seals the hollow fibers to the case and the inner core and seals the area between the exterior of the hollow fibers. This procedure allows both ends of fiber bundle 16 to be potted at the same time, thus resulting in a considerable savings of time and equipment utilization in the construction process.

Figure 13:
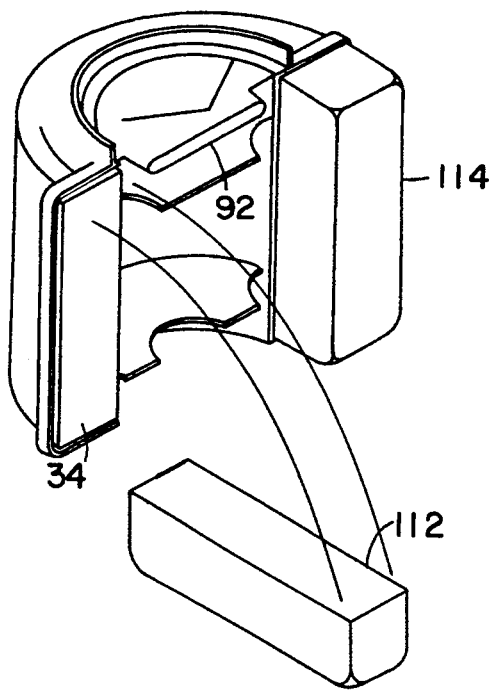
Figure 14:
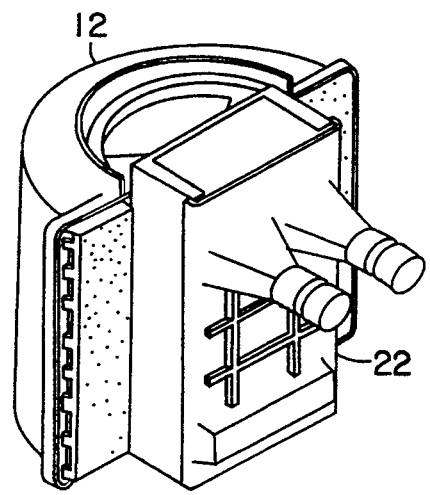
Figure 15:
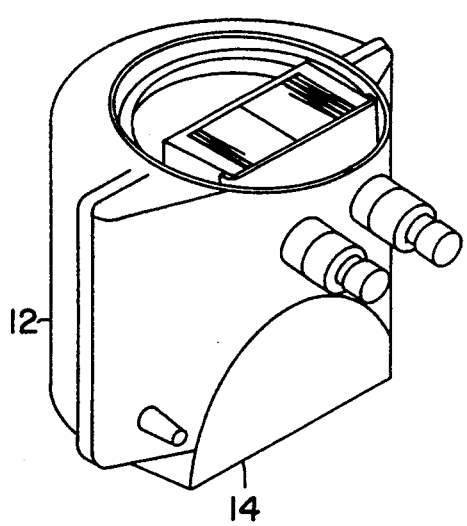
Figure 16:
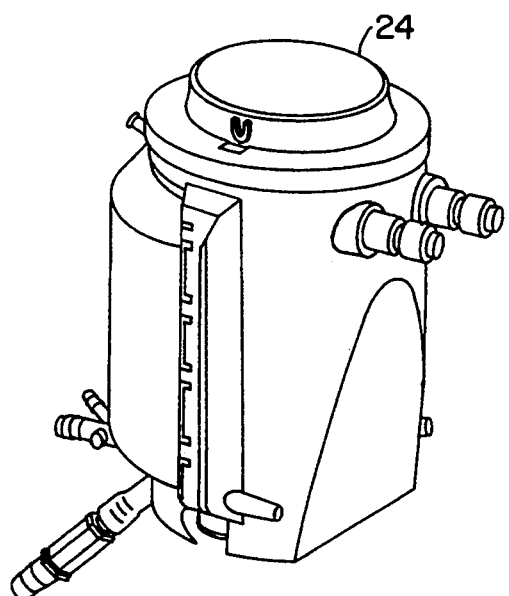

Once the potting compound has cured, potting caps 104 and 106 are removed and the potted ends 112 and 114 of the fibers are trimmed back far enough to expose the interiors of the fibers(FIG. 13). The potted areas 34 which remain seal the oxygenating chamber 35 at both ends of the fiber bundle 16. Heat exchanger 22 is then attached to inner core 18 and case portion 12 (FIG. 14). Case portion 14 and top end cap 24 are then added to complete the construction of blood oxygenator 10 (FIGS. 15 and 16).

From the foregoing detailed description of the invention, in should be apparent that a mass transfer device having a hollow fiber bundle and method of construction thereof has been disclosed. Although a particular embodiment of the invention has been disclosed herein, in detail, this has been done for the purpose of illustration only, and is not intended to be limiting with respect of the scope of the appended claims, which follow. In particular, it is contemplated by the inventors that various substitutions, alterations and modification, may be made to the embodiments of the invention described herein without departing from the scope of the invention as defined by the claims. For example, the choice of materials or variations of the size and shape of the hollow fibers or hollow fiber bundle are believed to be a matter of routine for a person of ordinary skill in the art with knowledge of the embodiments disclosed herein. Likewise, although the embodiments disclosed relate primarily to mass transfer devices for oxygenating blood, the present invention could be used for other applications such as dialyzers.

We claim:

1. A method of making fiber bundles for use in hollow fiber separation devices comprising the sequential steps of:
   winding one or more hollow fibers circumferentially around a supporting core, said supporting core including a first core section and a second core section which define a longitudinal axis, then
   mounting first and second outer casing sections adjacent the exterior of said hollow fibers, then
   cutting through said hollow fibers in at least two circumferentially spaced locations such that said hollow fibers are divided into a plurality of fiber bundles including a first fiber bundle lying generally between said first outer casing and said first core section and a second fiber bundle lying generally between said second outer casing and said second core section, each of said first and second fiber bundles having the interior of said fibers exposed along a first end and a spacially separated second end, whereby both said first and second fiber bundles may be used in hollow fiber separation devices.

2. The method of claim 1 wherein said supporting core is substantially cylindrical.

3. The method of claim 1 wherein the step of cutting through said hollow fibers is made in a direction substantially parallel to the longitudinal axis of said supporting core.

4. The method of claim 1 wherein the step of cutting through said fibers is made in a direction substantially coinciding with a plane through the longitudinal axis of said core such that said first and second fiber bundles are substantially identical in size and shape.

5. A method of making a hollow fiber separation device comprising the sequential steps of:
   winding at least one hollow fiber around a supporting core, said supporting core defining a longitudinal axis extending therethrough, then
   mounting an outer casing adjacent the exterior of said hollow fibers, then
   cutting said hollow fibers in at least two circumferentially spaced locations to form a fiber bundle having a first cut end at which the interiors of a first end of said hollow fibers are exposed and a second cut end at which the interiors of a second end of said hollow fibers are exposed, then
   sealing between the first cut ends of said hollow fibers in said fiber bundle,
   sealing between the second cut ends of said hollow fibers in said fiber bundle, such that the seal between the first and second cut ends of said fiber bundle and said core section and said casing section together define a molecular transfer chamber, then
   coupling first fluid inlets to the interior of said hollow fibers at the first cut ends of said hollow fibers in said fiber bundle and coupling first fluid outlets to the interior of said hollow fibers at the second cut ends of said hollow fibers in said fiber bundle,
   coupling second fluid inlets to said molecular transfer chamber for allowing said second fluid to enter said molecular transfer chamber and coupling second fluid outlets to said molecular transfer chamber for allowing said second fluid to exit from said molecular transfer chamber.

6. The method of claim 5 wherein the step of cutting results in said fiber bundle being shaped such that the first and second cut ends of said fiber bundle and the longitudinal axis of said supporting core lie generally in a common plane.

7. The method of claim 5 wherein the step of cutting through said hollow fibers is made in a direction substantially parallel to the longitudinal axis of said supporting core.

8. The method of claim 5 wherein the steps of sealing between the first and second cut ends of said hollow fibers are performed simultaneously.

9. A method of making hollow fiber bundles for use in oxygenators, the oxygenators having an outer casing and a core section between which is an oxygenation chamber which houses the fiber bundle, a gas inlet operatively coupled to the interior of the hollow fibers at a first end of the fiber bundle and a gas outlet operatively coupled to the interior of the hollow fibers at a second end of the fiber bundle which is spacially separated from the first end of the fiber bundle, a blood inlet and a blood outlet operatively coupled to the oxygenation chamber for allowing blood to enter and exit from the oxygenation chamber, the method comprising: the sequential steps of
   winding one or more hollow gas permeable fibers around a support core, said support core including a first core section and a second core section and defining a longitudinal axis, then
   mounting a first outer casing and a second outer casing adjacent to said hollow gas permeable fibers such that said hollow gas permeable fibers are between said first and second outer casings and said support core, then
   cutting said through said hollow gas permeable fibers in at least two circumferentially spaced locations such that said fibers are divided into a first hollow fiber bundle lying generally between said first outer casing and said first core section and a second hollow fiber bundle lying generally between said second outer casing and said second core section, whereby said first and second fiber bundles may be used in separated oxygenators.

10. The method of claim 9 wherein the step of cutting through said fibers is made in a direction substantially coinciding with a plane through the longitudinal axis of said core such that said first and second fiber bundles are substantially identical in size and shape.

11. The method of claim 9 wherein the step of cutting through said hollow fibers is made in a direction substantially parallel to the longitudinal axis of said support core.

12. A method of making an oxygenator comprising the sequential steps of:
   winding at least one gas permeable hollow fiber around a supporting core, said supporting core having a longitudinal axis, then
   mounting an outer casing around the exterior of said hollow fibers, then
   cutting said hollow fibers in at least two circumferentially spaced locations to form a fiber bundle having a first cut end at which the interiors of a first end of said hollow fibers are exposed and a second cut end at which the interiors of a second end of said hollow fibers are exposed, then
   sealing between the first cut ends of said hollow fibers in said fiber bundle,
   sealing between the second cut ends of said hollow fibers in said fiber bundle, such that the seal between the first and second ends of said fiber bundle and said core section and said casing section together define an oxygenation chamber, then coupling gas inlets to the interior of said hollow fibers at the first cut ends of said hollow fibers in said fiber bundle and coupling gas outlets to the interior of said hollow fibers at the second ends of said hollow fibers in said fiber bundle, coupling blood inlets to said oxygenation chamber for allowing blood to enter said oxygenation chamber and coupling blood outlets to said oxygenation chamber for allowing blood to exit from said oxygenation chamber.

13. The method of claim 12 wherein the step of cutting results in said fiber bundle being shaped such that the first and second cut ends of said fiber bundle and the longitudinal axis of said supporting core lie generally in a common plane.

14. The method of claim 12 further comprising mounting a heat exchanger within said outer casing, said heat exchanger provided with a blood entry and blood exit, the blood exit from said heat exchanger positioned and arranged in fluid communication with said blood inlet.

15. The method of claim 12 wherein the step of cutting through said hollow fibers is made in a direction substantially parallel to the longitudinal axis of said supporting core.

16. The method of claim 12 wherein the steps of sealing between the first and second cut ends of said hollow fibers are performed simultaneously.

17. A method of making an oxygenator comprising the sequential steps of:

winding at least one gas permeable hollow fiber around a supporting core, said supporting core including first and second core sections and defining a longitudinal axis, then mounting an outer casing around the exterior of said hollow fibers, said outer casing having a first casing section and a second casing section, then cutting through said hollow fibers in at least two circumferentially spaced locations such that said fibers are divided into a plurality of fiber bundles including first and second fiber bundles, said first and second fiber bundles each having a first cut end at which the interiors of a first end of said hollow fibers are exposed and a second cut end at which the interiors of a second end of said hollow fibers are exposed, said first fiber bundle lying generally between said first casing section and said first core section and said second fiber bundle lying generally between said second casing section and said second core section, said first fiber bundle, said first core section and said first casing section together forming a first oxygenator, said second fiber bundle, said second core section and said second casing section together forming a second oxygenator, then sealing between the first ends of said hollow fibers in said first and second fiber bundles, sealing between the second ends of said hollow fibers in said first and second fiber bundles, the sealed areas at the cut ends of said hollow fibers in said first fiber bundle, said first core section and said first casing section together defining a first oxygenation chamber in said first oxygenator, the sealed areas at the cut ends of said hollow fibers in said second fiber bundle, said second core section and said second casing together defining a second oxygenation chamber in said second oxygenator, then coupling gas inlets to the interior of said hollow fibers at the first cut ends of said hollow fibers in said first and second hollow fiber bundles and coupling gas outlets to the interior of said hollow fibers at the second cut ends of said hollow fibers in said first and second fiber bundles, coupling blood inlets to said first and second oxygenation chambers for allowing blood to enter said oxygenation chambers and coupling blood outlets to said oxygenation chambers for allowing blood to exit from said oxygenation chambers.

18. The method of claim 17 wherein the step of cutting results in said first and second fiber bundles being shaped such that the first and second cut ends of said first and second fiber bundles and the longitudinal axis of said supporting core lie generally in a common plane.

19. The method of claim 17 wherein the step of cutting through said hollow fibers is made in a direction substantially parallel to the longitudinal axis of said supporting core.

20. The method of claim 17 wherein the steps of sealing between the first and second cut ends of said hollow fibers are performed simultaneously.

21. The method of claim 17 further comprising mounting a heat exchanger within said outer casing, said heat exchanger provided with a blood entry and blood exit, the blood exit from said heat exchanger positioned and arranged in fluid communication with said blood inlet.

* * * * *